United States Patent [19]

Flynn

[11] Patent Number: 4,609,921
[45] Date of Patent: Sep. 2, 1986

[54] DIGITAL MODULATION DEPTH DETECTOR

[75] Inventor: James M. Flynn, Cedar Rapids, Iowa

[73] Assignee: Rockwell International Corporation, El Segundo, Calif.

[21] Appl. No.: 550,268

[22] Filed: Nov. 9, 1983

[51] Int. Cl.⁴ .............................................. G01S 1/18
[52] U.S. Cl. .................................... 343/411; 343/413
[58] Field of Search ....................... 343/411, 410, 413

[56] References Cited

U.S. PATENT DOCUMENTS 3,531,804  9/1970  Perkins ........................... 343/411 X
3,560,979  2/1971  Boelter .............................. 343/413
3,716,864  2/1973  Stover ............................... 343/411
3,967,278  6/1976  Buehler et al. ..................... 343/411
3,976,267  8/1976  Meyer et al. .................... 343/411 X Primary Examiner—Theodore M. Blum
Assistant Examiner—John B. Sotomayor
Attorney, Agent, or Firm—Richard W. Anderson; Robert C. Mayes; George A. Montanye

[57] ABSTRACT

An improved system for digital analysis of a composite modulated signal to determine difference in depth of modulation is disclosed. The system is useful, for example, in developing deviation signals for use in an ILS autoland system.

2 Claims, 3 Drawing Figures

DIGITAL MODULATION DEPTH DETECTOR

This invention relates generally to instrument land system (ILS) receivers and more particularly to an improved system for digitally processing composite 90/150 Hz signals developed by glide slope and localizer receivers to develop deviation steering signals by means of which an aircraft may be kept on a localizer or glide slope beam.

Both glide slope and localizer receivers demodulate a received carrier which is compositely modulated with 90 and 150 Hz tones. When the aircraft is on a defined glide slope or localizer path, the modulation depth of each of the 90 and 150 Hz modulating signals is equal and the difference in amplitude of the two demodulated tones is zero. As the aircraft deviates above or below a defined glide path or to the left or right of a defined localizer path, one or the other of the 90 and 150 Hz modulation components exceeds the other and thus the difference therebetween is utilized as a deviation signal which may be used to steer the aircraft back onto the desired path.

Analog glide slope and localizer receivers thus are known to employ bandpass filters to which a demodulated composite 90/150 Hz signal is applied and by means of which the 90 and 150 Hz components of the composite demodulated signal are separated. The separated tones are then rectified with the difference in magnitude between the rectified 90 and 150 Hz signals comprising a deviation signal and the sum being utilized to develop an overall signal strength by means of which warning flag annunciators may be controlled.

With the advent of digital signal processing, the disadvantages of analog circuitries to perform bandpass filtering, rectification, addition and subtraction have been obviated by the inherent accuracy and improved mean time between failure made possible by digital processing techniques. One such known digital ILS receiver, commercially available as the Rockwell International-Collins ILS700, applies the composite 90/150 Hz signal from a glide slope or VOR receiving demodulating circuitry to an analog-to-digital converter and the algorithm by means of which the composite 90/150 Hz demodulated signal develops a deviation output signal is accomplished by means of a microprocessor which accomplishes filtering, rectification, addition, subtraction, and division using digital techniques rather than using analog circuitries to develop the desired deviation output signal.

Accordingly it is an object of the present invention to provide an improved digital deviation detection algorithm by means of which jitter in the least significant bit outputs of the deviation signal developed is appreciably diminished.

It is a further object of the present invention to effect anti-aliasing subroutine in such a manner that storage requirements are minimized.

A still further object of the present invention is the provision of an improved digital analysis algorithm by means of which reduction in drift, skewing errors and noise are realized.

The present invention is featured in an improved ILS deviation output signal development algorithm wherein a more accurate low-pass filtering of the full wave rectified 90 and 150 Hz components of the input signal is effected prior to summing and differencing and anti-aliasing is effected upon a filtered dc level basis rather than on a full wave rectified tone basis.

These and other features and objects will become apparent upon reading the following description with reference to the accompanying drawings in which.

Figure 1:
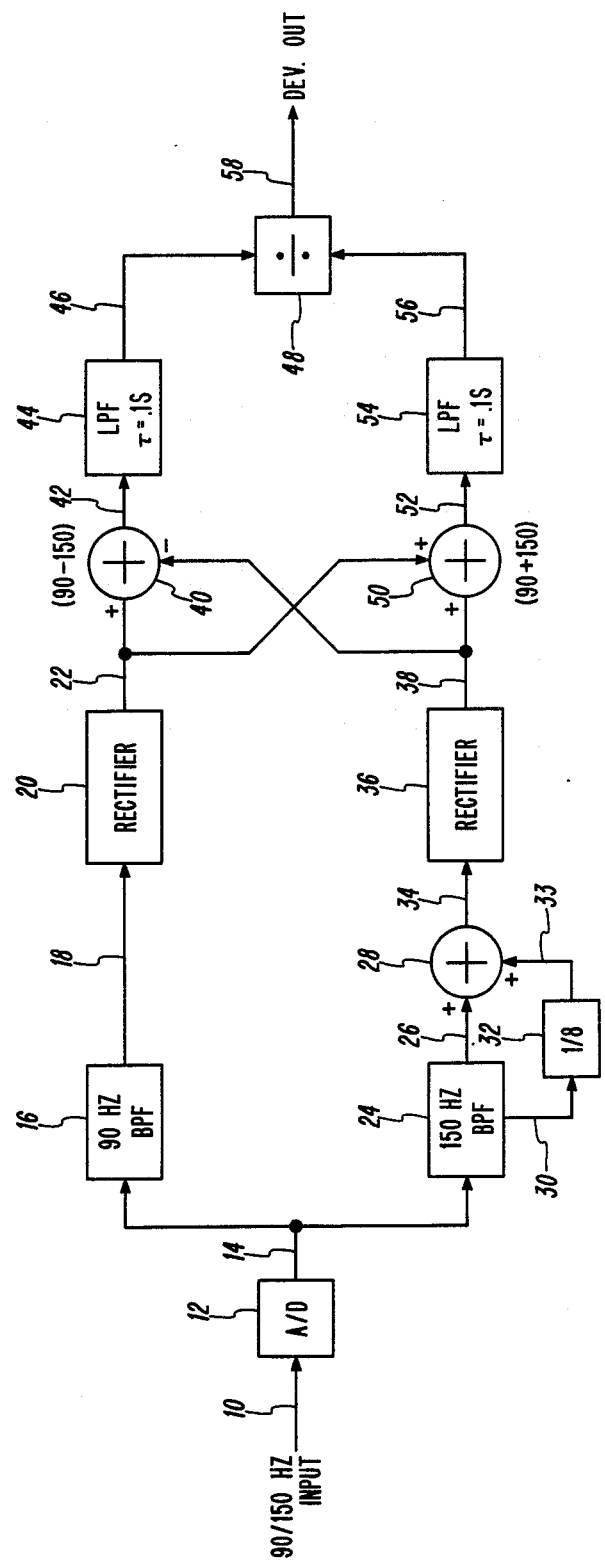
FIG. 1 is a block diagram of a prior art digital algorithm for obtaining a digital deviation output signal in an ILS receiver.

FIG. 1 shows a block diagram of the algorithm employed in the known digital ILS-700 ILS receiver. A composite 90/150 Hz input signal 10, as obtained from receiver demodulating circuitry, is supplied to an analog-to-digital converter 12 where, by known techniques, the composite input signal 10 is sampled and stored in the form of digital words representative of the magnitude of the composite input signal 10 as obtained from successive samples. The output 14 from analog-to-digital converter 12 is sequenced to a 90 Hz bandpass filter operation 16, with a filtered output 18 applied to a full wave rectifier operation 20 to provide an output 22 indicative of the full wave rectified 90 Hz component of the composite input signal. Similarly, the digital samples from analog-to-digital converter 12 are applied to a 150 Hz bandpass filtering operation 24. The output 26 from 150 Hz bandpass filtering operation 24 comprises the 150 Hz component of the composite input signal, and this output is also supplied as an input 30 through a ⅛ gain function 32, the output 33 of which is combined with the 150 Hz bandpass filter output 26 in summer 28 to provide an output 34 corresponding to the magnitude of the 150 Hz component of the composite signal increased by ⅛ to provide an anti-aliasing feature compensating for roll off induced in circuitry prior to the 150 Hz bandpass filtering operation. Each of the 90 and 150 Hz signals 18 and 34 are full-wave rectified in rectifier operations 20 and 36, respectively, to provide full-wave rectified 90 Hz output 22 and full-wave rectified 150 Hz output 38. The full-wave rectified outputs 22 and 38 are summed by summing operation 50 to provide an output 52 correspnding to the summation of full-wave rectified 90 and 150 Hz signal components. The same full-wave rectified output signals 22 and 38 are subtracted in subtracting operation 40 to provide an output 42 corresponding to the difference between the two full-wave rectified modulation components. The difference output 42 is then filtered by low-pass filtering operation 44 to provide a dc level 46 corresponding to the difference in amplitude between the two tones, while the sum of the two rectified tones at 52 is applied to a further low-pass filtering operation 54 to develop a dc level output at 56 corresponding to the sum of the magnitude of the two tones. The two dc levels 46 and 56 are supplied to a division operation at 48 to provide a normalized deviation output indicative signal 58.

Figure 2:
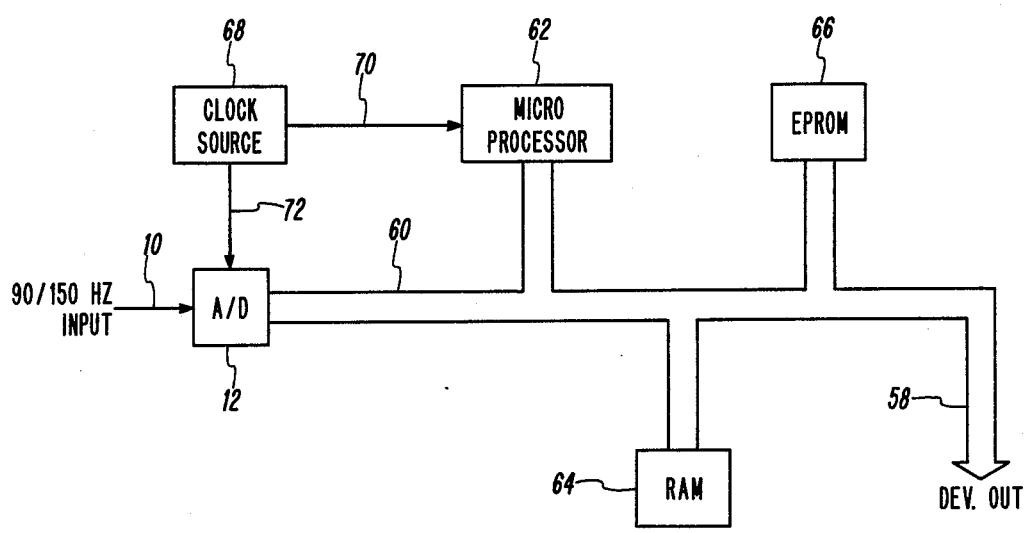
FIG. 2 is a functional block diagram of basic digital processing circuitry employable to realize the algorithms of FIG. 1 and FIG. 3.

With reference to FIG. 2, the digital processing algorithm of FIG. 1 may be embodied by an analog-to-digital converter 12 and microprocessor 62 which communicate by means of a digital bus 60. A clock source 68 provides iteration time definitive signals 70 and 72 to analog-to-digital converter 12 and a microprocessor 62 which communicates with bus 60. Also communicating with bus 60 is programmable READ ONLY memory means 66 and random access memory means 64. Deviation output is caused to appear as a digital output 58 from bus 60. State of the art programming techniques are incorporated in the general functional diagram of FIG. 2 by means of which digital processing techniques may be sequentially affected to accomplish the deviation signal development algorithm of FIG. 1.

The known algorithm depicted in FIG. 1 is noted to incorporate summing and differencing of full-wave rectified signals followed by filtering to obtain dc levels which are divided to provide the deviation indicative output 58. Because a digital implementation necessarily includes sampling of these full wave rectified signals to subsequently effect the summing and differencing operations, it has been found that a digital low-pass filtering routine on such sampled signals give rise to jitter and noise in the least significant bits of the digital output of the deviation signal subsequently developed. It has been further found that effecting the anti-aliasing operation directly on the output of the 150 Hz bandpass filtering subroutine gives rise to unnecessary storage requirements and operational steps in the digital operation.

Figure 3:
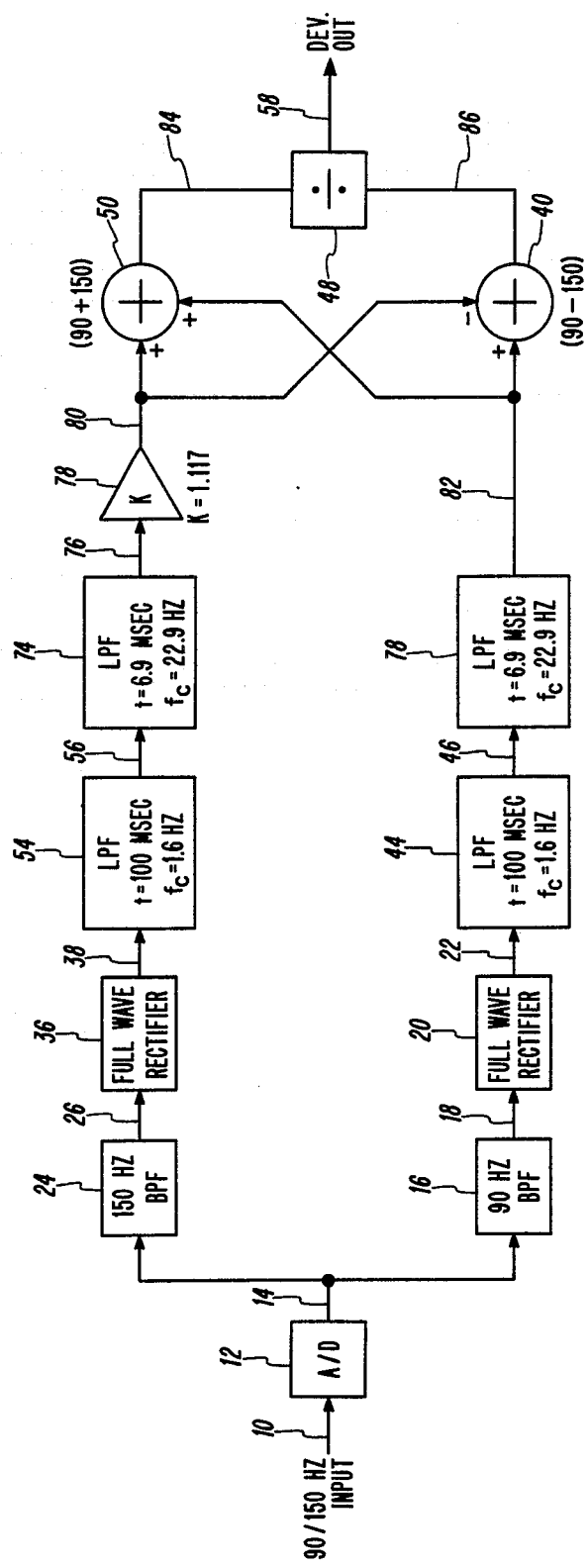
FIG. 3 is a functional block diagram of an improved algorithm for obtaining ILS deviation output signal in accordance with the present invention.

The improved algorithm for digitally developing a deviation output signal from a composite 90/150 Hz tone input is shown in the algorithm block diagram of FIG. 3. Digital operations of a similar nature in FIG. 3 are referenced as in the prior art algorithm of FIG. 1. Referring to FIG. 3, the demodulated composite 90/150 Hz tone input 10 is applied to analog-to-digital conversion operation 12 to provide a digital output 14 for application to 150 Hz bandpass filtering operation 24 and 90 Hz bandpass filtering operation 16. The 150 Hz bandpass filtered output 26 is applied to a full-wave rectification operation 36 to develop a full-wave rectified 150 Hz output at 38, while the output 18 from 90 Hz bandpass filtering operation 16 is applied to a full-wave rectifier operation 20 to provide an output 22 corresponding to a full-wave rectified 90 Hz tone component. As opposed to the above-discussed prior art algorithm, which performs summing and differencing operations on the output of the full-wave rectification operations, in accordance with the present invention the full-wave rectified outputs from rectifier operations 36 and 20 are applied to low-pass filtering operations prior to the summing and differencing operations from which the deviation output is subsequently obtained. Thus the output 38 from full-wave rectifier operation 36 is applied through a first low-pass filtering operation 54 where $\lambda = 100$ milliseconds and $f_c = 1.6$ Hz. The output 56 from low-pass filtering operation 54 is applied to a subsequent low-pass filtering operation 74 where $\lambda = 6.9$ milliseconds and $f_c = 22.9$ Hz. The anti-aliasing feature to compensate for roll-off induced in circuitry prior to the 150 Hz bandpass filtering operation is accomplished by applying the output 76 from low-pass filtering operation 74 through a gain operation where the filtered signal 76 is multiplied by 1.117 (1⅛), with the output 80 from the gain operation 78 being applied to the summing and differencing operations 50 and 40.

The composite digitial output from analog-to-digital converter 12 is applied in the lower depicted channel to a 90 Hz bandpass filtering operation 16, the output 18 of which is applied to a full-wave rectification operation 20 to provide a full-wave rectified 90 Hz tone indicative signal to low-pass filtering operation 44, the output 46 of which is applied to a further low-pass filtering operation 78. Low-pass filtering operations 44 and 78 utilize the same $\lambda$ and $f_c$ as those in the 150 Hz operational channel. The output 82 from low-pass filtering operation 78 is then applied to the subsequent summing and differencing operations 50 and 40 from which the deviation output signal 58 is developed by a divisional operation at 48.

Significantly, the improved digital algorithm in accordance with FIG. 3 develops an appreciably less noisy deviation output signal 58. Here it is noted that the full-wave rectified outputs 38 and 22 are first low-pass filtered and then subsequently summed and differenced. In the prior art algorithm of FIG. 1, full-wave rectified signals are first summed and differenced and then subsequently low-pass filtered. According to the present invention, it has been found that first converting the full-wave rectified tones to dc, by utilizing integrative digital techniques to accomplish low-pass filtering, permits the summing and differencing of dc levels rather than full-wave rectified tones, and that the least significant bits of the digital deviation output subsequently developed are of improved accuracy and appreciably more stable than in the prior art technique. Further, by accomplishing the anti-aliasing function (multiplying by a gain factor of 1.117) on dc level signals, rather than operating on the output of the 150 Hz bandpass filtering operation at 24, permits a reduction in the required RAM storage in the digital processing. The prior art technique of operating on the output of the 150 Hz bandpass filter operation to effect anti-aliasing requires storing bandpass filter output and also bandpass filter output plus ⅛ bandpass filter output, thus imposing extra time requirement on the bandpass filtering subroutine.

The present invention thus provides a means for more accurately providing a digital modulation depth detection operation. By digitally bandpass filtering the 90 Hz and 150 Hz components of the composite deviation signal followed by the determination of the magnitude of each tone through rectification integration and subsequent taking of the normalized difference between magnitudes, the algorithm in accordance with the present invention provides a digital analysis of a composite modulated signal and significantly reduces drift, skewing errors and noise in the deviation detection system. The system herein described significantly reduces jitter in the least significant bit output of the digital deviation output signal provided by the algorithm as compared to known prior art algorithms.

Although the present invention has been described with respect to a particular embodiment thereof, it is not to be so limited as changes might be made therein which fall within the scope of the invention as defined in the appended claims.

I claim:

1. The method for digitally determining the difference in depth of modulation between first and second tone modulation signals as represented by composite first and second tone modulations on a common carrier, comprising the sequential steps of:
    (1) converting the an analog signal representing said composite tone modulation to a digital signal,
    (2) digitally bandpass filtering the digital signal of step (1) to obtain first and second digital signals respectively definitive of said first and second tone modulation components,
    (3) digitally full-wave rectifying each of said first and second tone modulation components,
    (4) digitally low-pass filtering each of the full-wave rectified tone modulation components of step (3)

and digitally multiplying the higher frequency one of the low-pass filtered modulation components obtained by a predetermined gain factor in excess of unity, (5) digitally obtaining the sum and difference of each of the low-pass filtered modulation components of step (4), and (6) digitally dividing the difference obtained in step (5) by the sum obtained in step (5) to provide a digital output representing the difference in depth of modulation between said first and second tone modulation components.

2. The method of determining the difference in depth of modulation as defined in claim 1, wherein said first and second tone modulation complnents are 90 Hz and 150 Hz respectively.

* * * * *